United States Patent [19]

Zimmerman

[11] Patent Number: 5,139,566
[45] Date of Patent: Aug. 18, 1992

[54] GEOTEXTILE HAVING SOIL TREATMENT COMPOUND AND METHOD

[75] Inventor: Leon H. Zimmerman, Nashville, Tenn.

[73] Assignee: Reemay, Inc., Old Hickory, Tenn.

[21] Appl. No.: 453,004

[22] Filed: Dec. 18, 1989

Related U.S. Application Data

[63] Continuation of Ser. No. 97,543, Sep. 15, 1987, abandoned.

[51] Int. Cl.⁵ ............................................... B21D 3/02
[52] U.S. Cl. .................... 71/121; 71/DIG. 1; 264/251; 264/257; 264/273
[58] Field of Search ............... 428/139, 198, 224, 289, 428/290; 71/DIG. 1, 27, 29, 64.13, 903, 904, 121; 47/9

[56] References Cited

U.S. PATENT DOCUMENTS

| | | | |
|---|---|---|---|
| 1,971,504 | 8/1934 | Pratt | 71/64.13 |
| 2,023,270 | 12/1935 | Fischer | 71/904 X |
| 3,831,317 | 8/1974 | Porte | 71/901 X |
| 3,864,114 | 2/1975 | Green | 71/DIG. 1 |
| 4,173,844 | 11/1979 | Knolle et al. | 47/56 |
| 4,240,817 | 12/1980 | Takizawa et al. | 71/29 |
| 4,350,678 | 9/1982 | Palvarini et al. | 71/DIG. 1 |
| 4,405,360 | 9/1983 | Cardarelli et al. | 71/DIG. 1 |

FOREIGN PATENT DOCUMENTS

| | | | |
|---|---|---|---|
| 47-18956 | 9/1972 | Japan | 264/251 |
| 47-39308 | 10/1972 | Japan | 264/251 |
| 0126402 | 8/1982 | Japan | 71/64.13 |
| 2111388 | 7/1983 | United Kingdom | 71/64.13 |

*Primary Examiner*—Ferris Lander
*Attorney, Agent, or Firm*—Juettner Pyle & Lloyd

[57] ABSTRACT

A geotextile having a soil treatment compound includes a porous sheet having a plurality of spaced nodules of composite material secured to the sheet. The nodules are composed of a soil treating agent and a binder which is injected through the sheet and solidified, such that the sheet is enmeshed by the nodules.

13 Claims, 1 Drawing Sheet

GEOTEXTILE HAVING SOIL TREATMENT COMPOUND AND METHOD

This is a continuation of copending application Ser. No. 07/097,543 filed on Sept. 15, 1987 and now abandoned.

BACKGROUND OF THE INVENTION

This invention relates to a porous sheet material having a chemical agent applied thereto for the purpose of releasing the agent into the soil on a gradual or long-term basis.

Various methods have been proposed for treating soil for controlling or regulating the growth of plant or animal life. If the chemical agent is applied directly to the soil, however, the effects are temporary, since the chemical tends to be washed away or degraded. A particular serious problem is the long term control of plant root growth in certain locations such as beneath remote power transmission lines or into areas containing toxic materials. Many herbicides are useful for these purposes, including those described in U.S. Pat. Nos. 3,111,403, 3,257,190 and U.S. Pat. No. 4,101,582. A particularly useful herbicide is N,N-di-n-propyl-4-trifluoromethyl-2-6-dinitroaniline, which is known by the generic name trifluralin and sold under the trademark "TREFLAN."

In order to accomplish long term control of plant growth and root development, it is known to provide slow release systems for herbicidal and other soil treatment compounds. The herbicide or other compound may be incorporated or dispersed in a solid matrix of a water insoluble polymer such that the active compound is released very slowly, i.e., for periods for up to one hundred years. These slow release materials are typically prepared in the form of solid pellets which are deposited in the soil in a uniformly spaced manner. Manually positioning the individual pellets in the required pattern in the soil is time consuming and cost prohibitive. In addition, if there is nothing to hold the pellets in place, however, they tend to become displaced over a period of time, causing loss of control. Passage of water or soil disruption may cause movement of the pellets to adjacent areas, causing damage to useful plants or crops.

A geotextile is a porous sheet material which may be applied on or beneath the soil surface for a variety of purposes, for example, to block passage of sunlight or to control erosion, while allowing passage of water. These textiles are usually made from non-degradable materials such as polymers. Particular examples included non-woven spunbonded textiles made from filaments or fibers of polypropylene, such as products sold under the trademark "Typar." It would be desirable to incorporate slow release soil treating agents into geotextiles for the purpose of selectively treating soil in specific locations.

In order to be effective, the slow release material must have a certain minimum size or cross section to provide a minimum length herbicide migration path. A second requirement is the precise relative positioning of the deposits in the soil to obtain a durable and impenetrable root barrier plane. Thus, for example, direct incorporation of a herbicide into the geotextile during manufacture or by applying a uniform coating onto a porous substrate is either not feasible or would not provide the required slow release feature.

A preferred slow release system comprises a herbicide such as trifluralin adsorbed into carbon black and dispersed in a matrix of polyethylene. An attempt was made to place uniform deposits of this mixture onto a spunbonded web of polypropylene. It was found that the herbicides generally have a much lower melting point than the time release polymer, causing loss of herbicide during application of the mixture in molten form. Also, it is very difficult to make the mixture adhere to the porous web even with the use of adhesives.

SUMMARY OF THE INVENTION

An object of this invention is to provide a porous geotextile with a soil treating chemical which will be gradually released over a period of time.

Another object of this invention is to provide a method of adhering spaced masses or nodules of soil treating materials to a porous substrate or web in a reliable manner and without the use of special adhesives.

The foregoing objectives are accomplished by applying a molten mass of the slow release material to a porous web in such a manner that material is forced through the web and allowed to cool and solidify. In this fashion, the deposited material entraps the porous web and is firmly bonded thereto.

Also, in order to prevent evaporation of the herbicide or other chemical agent during application of the molten mixture, a special technique is employed. The molten material is injected from an insulated nozzle through one side of a porous web. The other side of the web is provided with a chilled mold or chamber opposite the nozzle. The molten material flows through the web under pressure whereupon it is immediately chilled and solidified in the form of the mold. While the molten material is being injected, the porous web allows air to escape while retaining the molten mass under pressure until it has cooled.

A plurality of nozzles and chilled molds may be employed across the width of the web and the web may be sequenced to apply any desired spaced series of deposits or nodules of the chemical mixtures over the entire surface of the web.

The resulting web has several advantages, including the ability to conform to irregular ground surfaces. Also, the material may be supplied in convenient roll form and may be cut to the desired dimension. When the deposits on the web include a herbicide, the web may be installed beneath the ground to prevent penetration of roots beneath the web. The web may also be used as a wrap to protect objects such as pipes. Many other advantages will become apparent upon review of the following specification and claims.

THE DRAWINGS

DESCRIPTION OF THE PREFERRED EMBODIMENTS

Figure 1:
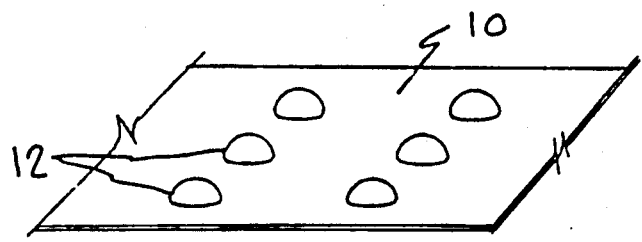
FIG. 1 is a perspective view of the product of the present invention.
Figure 2:
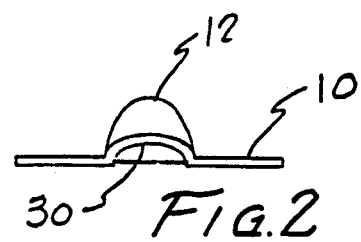
FIG. 2 is a vertical sectional view of a portion of the product shown in FIG. 1.

In general, the present invention contemplates the provision of a porous web or sheet 10 having a plurality of spaced nodules 12 of a slow release, soil treatment system bonded thereto, as shown in FIGS. 1 and 2. The sheet may be applied to the soil surface or beneath the soil surface for a variety of purposes, as will be described more fully herein.

The term "soil treatment agent" as used herein means a compound or mixture of compounds which, when added to the soil, are effective to control, regulate or promote the growth of plant or animal life in the soil. Conventional agents, for example, would include herbicides, fungicides, insecticides, nutrients, plant seeds, moisture absorbers, hormones, enzymes and the like. In the preferred embodiment, the agent is a herbicide, which may be used to prevent or control the growth of roots. A suitable class of herbicides are the dinitroanilines described in U.S. Pat Nos. 3,111,403, 3,257,190 and U.S. Pat. No. 4,101,582.

The porous web 10 is a flat porous flexible sheet of any desired dimensions. The sheet may be woven or non-woven but is preferably composed of materials which do not degrade or rot during contact with the soil over a period of time. A particularly suitable web is a spunbonded non-woven synthetic material, such as a material composed of overlapping filaments of a polymer such as polypropylene. One such material is sold under the trademarks "TYPAR" or "TEKTON."

The nodules or deposits 12 on the web 10 preferably comprise the soil treatment agent which is dispersed in a water insoluble solid binder or matrix in such a manner that the active agent will be continuously released over a relatively long period of time. During application, the binder is in the form of a liquid or liquid mixture which is capable of penetrating through the pores of the web. Upon application, the liquid is solidified in the desired shape as explained more fully herein.

Broadly, suitable binders or carriers for soil treatment agents include thermoplastic or curable materials. In the preferred embodiment, the binder is a thermoplastic polymer such as a polyolefin, polyester, polyvinyl chloride, or the like. In the case of a herbicide such as a dinitroaniline, the preferred carrier is a low density polyethylene. The carrier may also contain fillers or absorbent materials such as carbon black.

In use, the geotextile is applied to the soil to form a layer on or beneath the soil. The web 10 is flexible and conforms to irregularities or changing contours. When the agent is a herbicide, the sheet may be employed beneath power lines, at the edge of paved surfaces, around pipes, and over waste areas. Thereafter, the herbicide is released over a period of time and prevents penetration of roots through the treated web. Depending on the carrier employed for the herbicide, and the size of the nodules 12, effective amounts of herbicide will continue to be released for long periods of time, i.e., up to 100 years and beyond.

The process for making the product will now be described in connection with herbicides. Broadly, the method comprises the steps of injecting or forcing under pressure a quantity of a mixture of a liquid binder and active agent through one side of the porous web, and then allowing the mixture to solidify in the form of a discreet lump or nodule on the other side of the web. During solidification, the porous web in entrapped by the binder such that the resulting nodule is permanently enmeshed and attached to the web. As shown in FIG. 1, a multiplicity of lines and rows of spaced nodules may be applied to the web in order to provide overlapping zones of release of the herbicide.

Figure 3:
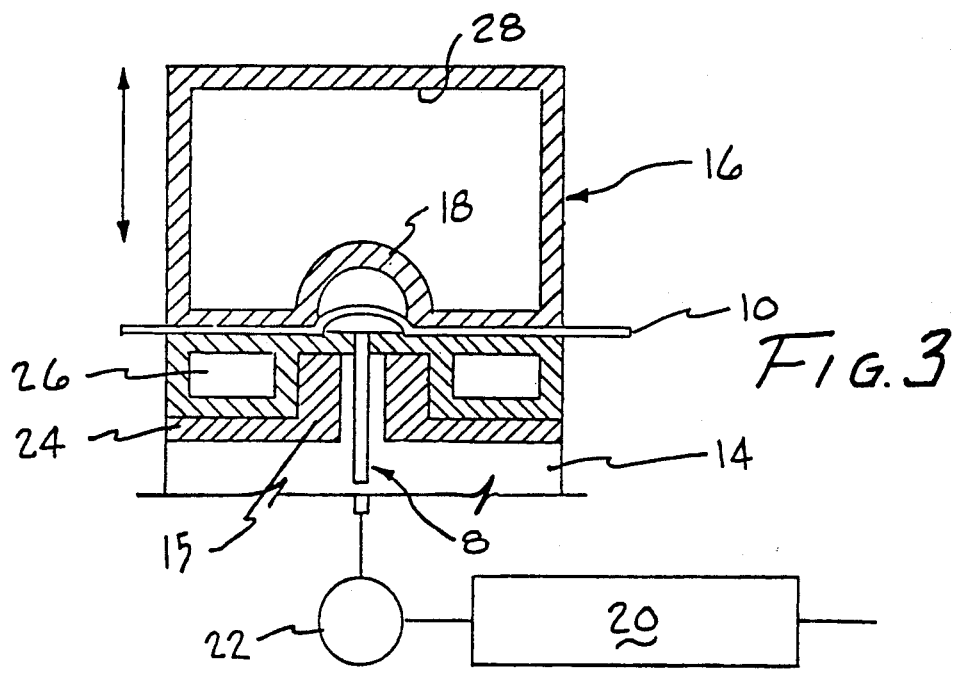
FIG. 3 is a vertical sectional view of apparatus useful in carrying out the present invention.

In the preferred embodiment, as shown in FIG. 3, the porous web 10 is disposed horizontally, and the carrier and active agent mixture is injected under pressure through the lower surface of the web through a nozzle 14. A mold, generally indicated at 16, has an open cavity 18 and is pressed against the other side of the web 10, with the cavity 18 facing the nozzle 14 and in register therewith. As the liquid mixture is injected through the porous web 10, it fills the cavity. The porous web allows air to escape but chilled surfaces of the mold solidify and retain the liquid. After the liquid has solidified, the mold 16 may be raised as shown by the arrow, and the web 10 may be moved to a new position to receive an additional deposit.

In the case of a herbicide, the herbicide is mixed with a thermoplastic carrier such as polyethylene and heated under pressure until the carrier becomes liquid. This may be accomplished with the use of a heated pump or extruder 20 having the outlet end thereof connected to the nozzle 14 after passing through a meter pump 22. In order to provide support for the underside of the web 10 during injection, an apertured plate 24 which may include chill chambers 26 with a planar surface is provided, with the nozzle 14 extending through the aperture and being insulated at 15. Also, in the case of thermoplastic materials, the mold 16 may have a circulation chamber 28 or other means for cooling, such as by passage of cold water. This allows rapid solidification of liquid mixture and reduces dwell time.

There are several important benefits in the use of a thru-web injection and molding technique. As the hot liquid mixture is injected through the web, as shown in FIG. 3, the liquid pressure causes the web 10 to deform or bulge at 30 toward the mold cavity, as shown in FIG. 2. As the mixture solidifies, the web is securely entrapped by the solidified mixture, and the resulting nodule 12 is permanently attached to the web, with the web enmeshed in the solid nodule. If the hot liquid was merely deposited on the surface of the web, the mixture would solidify but would not adhere to the web.

A second benefit is that the use of an opposed mold cavity allows the final shape of the nodule to be precisely controlled. The size and shape of the nodule is important in determining the rate of discharge of the herbicide from the polymer mass. As shown, the nodule is preferably dome shaped.

Finally, the use of injection into a cooled mold assures that the dispersion between the polymer and herbicide will remain uniform. The melting point of herbicides is usually much lower than the melting point of the polymer. Without the use of pressure and rapid cooling the herbicide would tend to escape from the heated mixture or migrate toward the outer surface and cause voids. The present method allows for system pressure to be maintained until the nodule has solidified.

Figure 4:
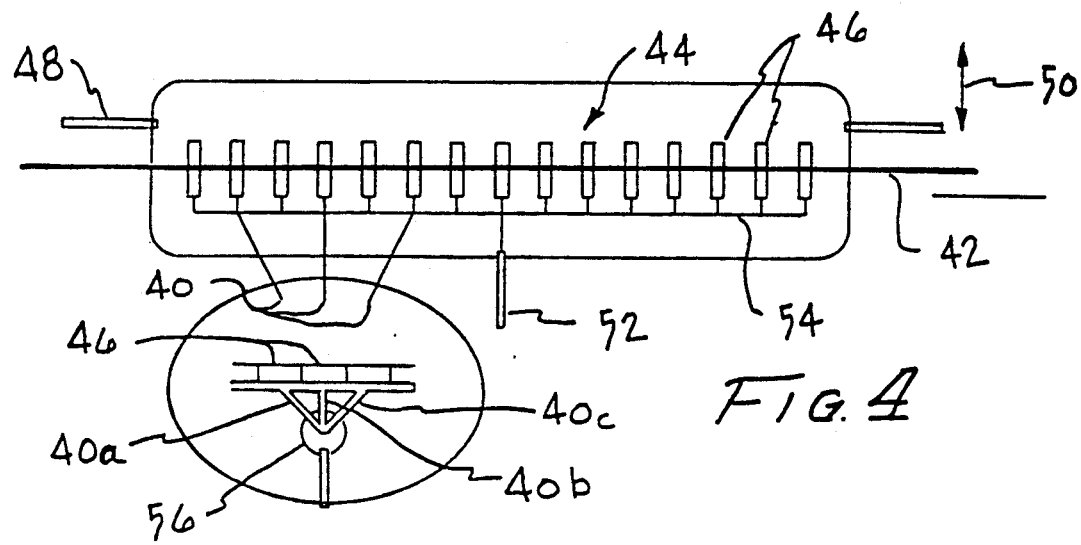
FIG. 4 is a schematic side view of another apparatus for carrying out the invention in a continuous fashion.

FIG. 4 schematically illustrates an apparatus for commercial production of the product described herein. Rows of spaced nozzles, 40 in groups of three, 40a, 40b and 40c, are disposed across the width of the web 42 to be treated. A chilled form casting 44 having a plurality of cavities such as 46 and chilled with water via supply line 48 is provided in registration with the nozzles 40. The casting 44 reciprocates vertically as indicated by the arrow at 50. In the up position the web 42 is moved in the direction indicated by the arrow and moves the length of the casting to expose a new area to be injected. In the down position, the casting 44 sandwiches the web 42 and seals in registry with the nozzles 40. The molten composite material is supplied via a line 52 and is distributed via a manifold 54. A reciprocating rotary valve 56 controls the composite flow time to the nozzles 40, injecting the composite through the web 42 and filling the sealed cavities 46 forming and cooling the deposit. The web may then be rewound and transported in aconvenient fashion.

In further illustration of the invention, the following example is given.

EXAMPLE

A geotextile was prepared to provide control of root growth. The textile was a spunbonded, non-woven web of polypropylene. Herbicide slow release systems were prepared which contained by weight from about 25 to about 28 percent trifluralin, from about 12 to about 15 percent carbon black, and the remainder as low density polypropylene. One specific useful formulation is 26.6 percent trifluralin, 13.3 percent carbon black, and 60.1 percent low density polypropylene.

The foregoing mixture was heated to a temperature sufficient to melt the polypropylene, or about 160° C. The material was mixed and supplied under pressure of about 1000 psi to a nozzle, and a quantity was injected through the porous web filling the facing chamber of a chilled mold cavity.

In order to provide effective distribution, the deposits are spaced regularly or uniformly over the surface of the web. In order to achieve the desired release of herbicide over long periods of time, the spacing between adjacent nodules should be no greater than 1.5 inches. Also, the size of the nodule should be equal to or greater than ⅜ inch base diameter dome.

What is claimed is:

1. Method of preparing a porous web having an active slow release treatment agent incorporated therein, said method comprising the steps of preparing a liquid mixture of the active treatment agent and a binder for said agent, injecting the liquid mixture through one side of the porous web at a plurality of locations to form a plurality of spaced nodules of said mixture on the other side of the web, and solidifying the nodules to bond the nodules to the web.

2. The method of claim 1 wherein the binder is a solid at room temperature, and wherein the agent and binder mixture are heated prior to injection.

3. The method of claim 2 wherein the agent and binder mixture are cooled upon passage through the web.

4. The method of claim 1 wherein the liquid mixture is injected through one side of the porous web into mold cavities disposed on the other side of the web to provide solid nodules projecting from the other side of the web.

5. The method of claim 4 wherein the liquid mixture is injected through the web at a plurality of spaced locations to provide a plurality of spaced nodules bonded to said web.

6. The method of claim 1 wherein the binder comprises a thermoplastic polymer and the active treatment agent comprises a herbicide.

7. The method of claim 6 wherein the binder comprises polyethylene and the active treatment agent comprises a herbicide.

8. The method of claim 1 wherein the mixture comprises polypropylene, carbon black and a herbicide.

9. The method of claim 1 wherein said web is a non-woven, spunbonded material.

10. The method of claim 9 wherein said web is composed of polypropylene.

11. A geotextile containing an active treatment agent incorporated therein, said geotextile comprising a porous sheet of filamentary polymeric material, and a plurality of spaced solid nodules projecting from one side of the sheet, said nodules comprising said active treatment agent dispersed in a solid polymeric matrix, said nodules being held in permanent position on said sheet by having been injected through said sheet with a portion of each nodule bonded around the filaments of the sheet.

12. The geotextile of claim 11 wherein said porous sheet comprises a non-woven, spunbonded fabric.

13. The geotextile of claim 11 wherein said nodules comprise a mixture of herbicide, carbon black and a polymer binder.

* * * * *